United States Patent
Philar

(10) Patent No.: US 10,264,792 B2
(45) Date of Patent: Apr. 23, 2019

(54) HOLISTIC, COST EFFECTIVE METHOD FOR MANAGEMENT OF HUANG LONG BING (HLB), PHYTOPHTHORA GUMMOSIS, ASIAN CITRUS PSYLLID AND OTHER SERIOUS INFESTATIONS IN CITRUS AND OTHER CROPS

(71) Applicant: Uday Bhavanishankar Philar, Pune (IN)

(72) Inventor: Uday Bhavanishankar Philar, Pune (IN)

(*) Notice: Subject to any disclaimer, the term of this patent is extended or adjusted under 35 U.S.C. 154(b) by 0 days.

(21) Appl. No.: 15/304,872

(22) PCT Filed: Oct. 14, 2014

(86) PCT No.: PCT/IN2014/000654
§ 371 (c)(1),
(2) Date: Oct. 18, 2016

(87) PCT Pub. No.: WO2016/024282
PCT Pub. Date: Feb. 18, 2016

(65) Prior Publication Data
US 2017/0181438 A1   Jun. 29, 2017

(30) Foreign Application Priority Data
Aug. 10, 2014  (IN) .................. 2572/MUM/2014

(51) Int. Cl.
| | | |
|---|---|---|
| *C05G 3/02* | (2006.01) |
| *A01N 25/00* | (2006.01) |
| *A01N 25/08* | (2006.01) |
| *A01N 25/28* | (2006.01) |
| *A01N 59/00* | (2006.01) |
| *A01N 59/16* | (2006.01) |
| *A01N 59/20* | (2006.01) |
| *A01N 61/00* | (2006.01) |
| *A01N 63/00* | (2006.01) |
| *A01N 63/02* | (2006.01) |
| *A01N 63/04* | (2006.01) |
| *A01N 65/00* | (2009.01) |
| *A01N 65/03* | (2009.01) |
| *A01N 65/20* | (2009.01) |
| *C05F 11/08* | (2006.01) |

(52) U.S. Cl.
CPC ............. *A01N 59/16* (2013.01); *A01N 25/00* (2013.01); *A01N 25/08* (2013.01); *A01N 59/00* (2013.01); *A01N 59/20* (2013.01); *A01N 63/00* (2013.01); *A01N 63/04* (2013.01); *A01N 65/00* (2013.01); *A01N 65/20* (2013.01); *C05F 11/08* (2013.01); *C05G 3/02* (2013.01)

(58) Field of Classification Search
CPC ........ A01N 59/16; A01N 59/00; A01N 59/20; A01N 63/00; A01N 63/04; A01N 65/00; A01N 65/20; A01N 25/00; A01N 25/08; C05F 11/08; C05G 3/02
See application file for complete search history.

(56) References Cited

FOREIGN PATENT DOCUMENTS

WO   2011126832 A2   10/2011

OTHER PUBLICATIONS

Pettit, R. E. "Organic Matter, Humus, Humate, HumiC Acid, FulviC Acid, and Humin: Their Importance in Soil Fertility and Plant Health", Texas A&M University, 2004; http://www.humates.com/pdf/ORGANICMATTERPettit.pdf.*
Xiang Wang, Longquan Chen, Elmar Bonaccurso and Joachim Venzmer, "Dynamic Wetting of Hydrophobic Polymers by Aqueous Surfactant and Superspreader Solutions", Langmuir, 2013, 29, 14855-14864.*
Mukesh Kumar and Ram Singh, "Potential of Pongamia glabra Vent as an Insecticide of Plant Origin", Biological Agriculture & Horticulture, 2002, vol. 20, No. 1, pp. 29-50, Abstract only.*
Lynch, J.M. et al., "Rhizopshere," Encyclopedia of Life Sciences, May 2012, pp. 1-8.
Rouse, B. et al., "Monitoring Trees Infected with Huanglongbing in a Commercial Grove Receiving Nutritional/SAR Foliar Sprays in Southwest Florida," Proc. Fla. State Hort. Soc., 2010, vol. 123, pp. 118-120.
Powell, C.A. "Control and Management Strategy for Citrus Huanglongbing in USA," University of Florida, Jan. 14, 2014, pp. 1-21.
Pustika, A.B. et al., "Interactions between Plant Nutrition and Symptom Expression in Mandarin Trees Infected with the Disease Huanglongbing," Australasian Plant Disease Notes, 2008, vol. 3, pp. 112-115.

* cited by examiner

*Primary Examiner* — John Pak
*Assistant Examiner* — Nathan W Schlientz
(74) *Attorney, Agent, or Firm* — William J. Clemens; Shumaker, Loop & Kendrick, LLP

(57) ABSTRACT

Method of controlling infestation of citrus comprising the steps of: i) application of nanobiocide component-1 as a soil drench and foliar spray followed by simultaneous application of component-2 and component-4 followed by the application of component-3, as and when the citrus psyllid observed at threshold levels; ii) application of component-6 which is silicone based wetting and spreading agent cum penetrant mixed with components 3 and 5 and water as foliar spray; ii) finally applying component-5from the onset of flowering at 30-45 day intervals.

16 Claims, No Drawings

HOLISTIC, COST EFFECTIVE METHOD FOR MANAGEMENT OF HUANG LONG BING (HLB), PHYTOPHTHORA GUMMOSIS, ASIAN CITRUS PSYLLID AND OTHER SERIOUS INFESTATIONS IN CITRUS AND OTHER CROPS

FIELD OF INVENTION

The present invention relates to the general subject of controlling including management, preventing, removing and treatment mechanisms of the infestation of citrus. More particularly, the present invention relates to the method and kit using of a plurality of compositions in different dose forms which when applied to citrus are capable of controlling the disease of bacteria of the genus *Candidatus liberibacter asiaticus, Candidatus liberibacter africanum* which cause the disease known as Huanglongbing (HLB), *Phytophthora* Gummosis and the insect vector of HLB namely, various species of the citrus psyllid deemed to be the most destructive disease currently to affect citrus crops worldwide.

BACKGROUND ART

Like any living organism the plants are subjected to numerous environmental, both abiotic and biotic, stresses. Drought, soil salinity, alkalinity and extreme temperatures are included among the abiotic stresses. Among the biotic stresses are included pests as insects, arachnids and nematodes, and pathogens such as bacteria, viruses and fungi. All these biotic and abiotic factors, manmade and natural are working together to make the global farming situation a lot more difficult than it has ever been. Unfortunately the conventional approach to problem solving has not yielded the desired results. As a result of this, we are facing a situation where the world population is increasing by 1.7% pa and food production is stagnating for the last 6 years.

Plants are subject to a wide variety of fungal, viral and bacterial diseases and damage by insects. Fruit bearing plants, in particular citrus trees are subject several totally destructive diseases like root rot and gummosis caused by *Phytophthora citrophthora* and Huanglongbing/Citrus Greening (*Liberibacter asiaticus* (CGD), which is vectored by the Asian citrus psyllid (ACP), *Diaphorina citri Kuwayama*.

Citrus gummosis and Huanglongbing are particular problems for citrus crops as is the insect vector, Citrus Psyllid. Presently, Huanglongbing is prevalent worldwide throughout all the countries that produce citrus; there is no known or reported cure. The official, sometimes mandated, scientific worldwide recommendation is for trees identified as affected with Hunaglongbing to be removed and burned. In the case of *Phytophthora*, hundreds of thousands of acres of various crops worldwide have been destroyed because of the effects of this pathogen, which has been historically known to have caused mass human migration due to famine. Presently the only official recommendation by the scientific community is prophylactic by spraying chemical fungicides on the plant tissue of citrus trees, which has little or no effect because of the deep seated nature of the disease and the tendency of the pathogen to rapidly develop resistance and cross resistance to such fungicides. This results in growers being required to increase the dosage or frequency of application of the chemical fungicide with a devastating effect to the environment and raising costs of cultivation by as much as 40% as reported by studies conducted by the Universities of Florida and California.

Our studies reveal that the bacterial agent causing Huanglongbing has a symbiotic relationship with the Asian Citrus Psyllid, its main vector (as well as the African Citrus Psyllid—*Trioza eritreae*). The characteristic mottled yellowing of the foliage caused by this disease and the chemical signals released by the affected plant attract the insect in large numbers for feeding and egg laying. Upon ingestion of the bacteria infected plant sap, this insect flies off to healthier plants in the vicinity and rapidly infects healthy orchards. This insect has a reported flying radius of 1.5 kilometers and can therefore infect a large area. These pests are also carried by wind and storms over much larger distances and spread the disease to healthy areas so conventional methods of physical quarantine are eventually breached by this disease and no citrus growing region can be considered totally safe from this malaise.

These insects and their nymphs feed on young growing plant tissues and release toxins and possibly viruses causing these tissues to curl and deform and thereby stunting growth. Since it is the new tissues that ultimately yield the current season's crop, the combined effect of the diseases as well as the feeding activities of the insect can be devastating. Psyllids as well as their nymphs excrete a sweet fluid known as honey dew which covers the surface of the leaves. This attracts a fungus known as the sooty mould fungus (caused by several genera like *Capnodium, Cladosporium, Aureobasidium, Antennariella, Scoria, Lirnacinula*). This forms a black coating on the leaves preventing access to sunlight and thereby hampering photosynthesis. This reduces carbohydrate synthesis reducing availability of energy and weakens the diseased tree further. Another effect the HLB bacterium has on the infected psyllid is to increase its fecundity and egg laying. A single female psyllid is able to lay over 300 eggs and due to their early maturity, there can be as many as 4-5 generations of the insect developing in a single year with favourable climatic conditions, enough to cause an uncontrollable epidemic.

It would be desirable to have a cost effective alternative that would be eco friendly and can be applied to fruit bearing plants without causing a problem of excessive pesticides residues that can impact human health. A holistic system that can not only retard damage caused by fungal and bacterial diseases, insect vectors as well as the damage caused by their feeding while enabling farmers and growers to restore their orchards quickly to their prime health and yield potential.

While this pest can be and is controlled by several available chemical insecticides belonging to classes like organophosphorus, synthetic pyrethroids, neo nicotinoids and others, all these cause collateral damage to beneficial insects such as parasites and predators and are not amenable to eco friendly techniques like integrated pest management. They are also toxic to pollinators like honey bees and have been implicated in causing large scale death of this useful insect by causing Colony Collapse Disorder (CCD). This has resulted in restrictions on their use or the banning of many of these insecticides including neo nicotinoids by EU nations for certain applications in horticulture. It is necessary to point out that the indiscriminate use of chemical insecticides has resulted in the extinction or near extinction of honey bees in China and has seen the USA resorting to the unprecedented step of importing honeybees from Australia to tide over their shortage.

From what has been previously commented on the state of the art in the control of the psyllid vectors of the *liberibacter* bacteria which cause the HLB of the citrus, one reaches the conclusion that basically the control of HLB has conventionally relied on the use of insecticides. The biological alternative has been the use of the pyllid parasitic wasps, *Tamarixia radiata* and the *Tamarixia dryi*. Unfortunately, in Florida, neither the use of insecticides nor predators have prevented the establishment of HLB.

The danger for the soil, environment, plants, animals and people, that the excessive use of pesticides involves, has led the researchers to consider other strategies of protection of the crops. One of the possible strategies is the use of compositions that activate the natural defence mechanisms of the plants against the attacks of pathogens and pests, without implying the use of such compositions adverse effects on the soil, the environment, the plants themselves, animals or people. In this sense, we have been researching for 25 years, about the effect that the plant growth regulators could cause in the reinforcement of the natural defence mechanisms of the plants and, as a consequence, in the induction of resistance to pathogens and pests on the plants treated with said regulators. In these researches we have seen how certain type of plant growth regulators, the water soluble Vitamin K derivatives, was able to stimulate the natural defence mechanisms of the treated plants and as a result to induce resistance to the attacks of pathogens and pests. ["Compositions for inducing resistance to tracheomycosis in plants". Patent: WO 95/03702, published: 9 Feb. 1995]; ["use to compositions containing menadione for biostimulation of the plant mechanism in order to induce its resistance to pathogens and pests]. Patent: [95 ES-9500522, published: 16 Apr. 1999]

Another prior art WO96/28026 discloses application of compositions which contain as active components vitamin K3 and/or at least one of their water-soluble derivatives, preferably menadione sodium bisulfite (MSB), and/or at least one of their derivatives having a low water solubility, preferably menadione nicotinamide bisulfite (MNB), and are in the form of an aquous solution intended to biostimulate the metabolism of plants in order to induce their resistance to pathogens and pests and/or advance the blooming of plants. In a preferred embodiment, the compositions are sprayed on banana trees.

Application of a wide range of antibiotics has also been attempted to control HLB, however these have not found favour for two reasons:

a) Many of the antibiotics have proved to be toxic to citrus
b) Due to their low residual action, multiple applications are required which raises costs
c) The most effective manner of application of antibiotics through stem injection is laborious, time consuming and expensive making it impractical for large scale use. Injuries to the stem of the citrus plant due to injections can predispose them to secondary infection by other fungal and bacterial pathogens.

Secondary infections caused by the opportunistic infection by other soil dwelling pathogens and pests is quite common given the weakened state of the infested citrus crop. The mechanism of entry can be through root tips already damaged and killed by HLB. Inoculum of pathogens like *Phytophthora* exist in the soil in a weaker saprophytic state and also as their spores such as chlamydospores or zoo spores. These are activated when they come into contact with irrigation water and root hairs of the crop which release exudates and chemical signals that attract these pathogens.

Soil dwelling pathogenic nematodes (like *Tylenchulus, Pratylenchus, Xiphinema, Belonolaimus, Meloidogyne, Radopholus* and many others) also cause damage to the roots of citrus plants. If these are already weakened by HLB, their ability to meet the nutrient and water requirements of the tree is already seriously impaired. Secondary infestation by any soil pathogen or nematode can prove to be the tipping point that accelerates the death of the citrus tree.

CURRENT RECOMMENDATIONS AND DISADVANTAGES

Destruction of affected trees is the only recommendation for halting the spread of this disease since there is no known cure. The second measure is to control its vector. This is usually done by repeated sprays of toxic chemical pesticides which harm the environment and destroy natural enemies of this pest and increases costs of production by 40%.

These pests are reported to be increasingly resistant to the best known insecticides and magnify this resistance across generations.

Since this disease can survive on other plants like bay leaf, weeds like periwinkle and even some ornamentals, destruction of the affected citrus plants can have only a limited impact on the spread of this disease.

The interaction between this disease, its insect vector and plants shows how difficult it can be to control this complex problem with a single approach:

a. The pathogen lies undetected in the plant for 1-2.5 years, steadily increasing in numbers while the tree does not show any physical symptoms
b. Once its numbers increase to the extent that it begins to infect the tree and the symptoms are noticed, it begins to change the colour of the leaves to yellow which is attractive to the psyllid. The pathogen also releases certain chemicals which serve to attract the psyllid in large numbers.
c. The psyllids congregate, feed and lay eggs on the growing tips of the diseased tree. In the act of feeding, they ingest some of the bacteria which multiply even more rapidly in their guts.
d. The current practice of spraying chemical pesticides destroys their natural enemies like spiders, lace wings, *Tamarixia* wasps and beetles which could have kept numbers in check. This also serves to destroys pollinators like honey bees.
e. Soil application of pesticides destroys soil ecological balance and requires the application of substantially higher doses of pesticides.
f. Stem injection is labour intensive and requires specialised equipment to be used by trained professionals and is therefore very cumbersome and expensive. Injuries caused by stem injections predispose the crop to secondary infection by other diseases.
g. The only way to control the bacterium is by using antibiotics like streptocycline which have proven to be toxic to the citrus tree, so these cannot be recommended for field application on a large scale. The other problem with antibiotics is their easy biodegradability in nature to sub lethal levels, which means they have a limited residual action necessitating repeated use which make them economically prohibitive.
h. Another problem is the death of growing root tips and weakened resistance of the plant attracts yet another serious fungal pathogen of citrus known as *Phytophthora citrophthora* which begins to exert its own impact on the affected tree, further reducing its productive life. Secondary infestation by nematodes can also be a significant but largely unrecognised contributory factor for the accelerated demise of the diseased trees. We have observed farmers in North India for the last 4 years reduced to the point of uprooting their beloved orchards.

i. The current practices that rely on excessive use of chemical fertilisers and herbicides affect beneficial soil microbes which predispose the crop to disease.

j. Undesirable soil conditions caused by excessive application of flood irrigation together with poor soil structure are also direct causative factors behind increased *Phytophthora* incidence.

k. Since these diseases affect the ability of roots to draw nutrients, deficiency syndromes are common; leading to excessive application of micronutrients which can increase soil toxicity.

l. Uprooting orchards has a negative environmental impact of reducing tree cover and further accentuating global warming and soil erosion.

m. The recommendation to increase the density of planting raises costs tremendously.

n. Farmers in developing countries are reluctant to uproot their trees till they can harvest something from their orchards. Even if they destroy their orchards, and plant afresh, there is no guarantee that the trees will not get infected by the disease once again. It take 5-6 years for a tree to reach a reasonable level of production, so this cycle of replanting and uprooting is not a viable option for farmers anywhere in the world in the long term.

o. In order to combat the cycle of resistance to pesticides, companies come up with new and prohibitively priced products which further aggravate the farmer's problems and reduce their profits.

SUMMARY OF INVENTION

An innovative method as disclosed herein has taken into account all these and more intertwined factors which will enable farmers to control the entire complex problem in a cost effective and eco-friendly manner. This approach rapidly reverses the course of this deadly disease in a short span of time. This may appear to be simple but has been made possible only after painstaking research to come up with a robust, cost effective solution that can be easily understood and implemented by farmers. Since the disease itself is chronic in nature, only a sustained implementation of the system can help keep the disease at bay.

The disclosed method simultaneously helps controlling the other most important disease of this crop, Gummosis of Citrus caused by *Phytopthora citrophthora* as well as other diseases affecting other crops caused by soil borne pathogens. This system also helps control various species of the Citrus Psyllid like the Asian Citrus Psyllid *Diaphorina citri Kuwayama* and alleviates their symptoms of damage to restore the health of the crop.

By virtue of the ability of this method to control *Phytophthora* on citrus, this can be used to additionally control the disease incidence cause by this pathogen on other crops like: potato, tomatoes, egg plants, bell peppers, oil palm, durian, black pepper, blue berries, forest trees and many more. This system by implication might also be used for controlling difficult diseases caused by soil borne pathogens like *Rhizoctonia, Fusarium, Aspergillus, Macrophomina, Pythium, Scerotinia, Verticillium* etc. These can infest an array of crops like strawberry, cole crops, celery, spinach, cucumber, melons, squash, beans, peas and many others.

The disclosed system has 6 components. These components have never been used earlier in a proper sequence or in the combination as disclosed herein for the control of infestation of citrus by HLB and *Phytophthora* as also the citrus psyllid.

a) The first component comprises of a water based formulation containing 30-50 ppm of nano silver particles which is used in conjunction with 2.5% hydrogen peroxide or alone in microencapsulated form. This formulation can also comprise nano particles of copper in the same concentration (30-50 ppm) in place of hydrogen peroxide.

b) The second component is a consortium of plant growth promoting rhizosphere microbes which occur in nature. There no genetic modification done. The microbes comprise bacteria which fix Nitrogen (N), Phosphorus (P). Potassium (K), like *Pseudomonas fluorescens, Bacillus subtilis, Bacillus mycoides, Paecilomyces lilacinus, Metarhizium anisopliae*, Zinc solubilising bacteria and (the fungus) *Trichodema viride* and micropropagules of 6 different species of the endo mycorrhiza *Glomus* in a highly concentrated formulation. The species includes *Glomus mosseae, G. intraradices, G. aggregatum, G. microaggregatum, G. fasciculatum* and *G. etinucatum*.

The consortium of microbes as used herein, either as a single product or divided into 2 components containing varying mixtures of these organisms based on the soil analysis or requirements of the site to be treated which provides a high degree of flexibility of use under varying soil conditions. The various microbes are present in concentrations of between $1\times10^8$ or $1\times10^9$ per gram of the product. The micropropagules of mycorrhizae are incorporated at concentrations of 50,000 to 150,000 micropropagules per gram of the product.

c) The third component is a plant extract of a naturally occurring tree with known properties that control insect pests in an eco-friendly way wherein oil extracted from the seed of Karanj (*Pongamia glabra/Derris indica*) is used whose properties have been known since ancient times in India. The final formulation is an emulsifiable concentrate comprising 2% alkaloids extracted from the oil in semi purified form together with oil ranging from 25-35% formulated with commonly used petroleum solvents and emulsifiers in order to keep the cost low.

d) The fourth component is a slow release, granulated formulation comprising amino acids, sea weed extracts, humic and fulvic acids (which are extracted from vermi compost). This provides the microbes ideal conditions to proliferate rapidly and alter the soil characteristics to favour root growth and keep pathogens away. Slow release is ensured by incorporating these constituents in double roasted bentonite granules with a coating of any natural polysaccharide or polymer natural or synthetic known to persons skilled in the art which dissolves very slowly on contact with soil moisture. The moisture absorption by the surface of the granule and availability of nutrients within also provides a suitable micro climate for the survival and rapid multiplication of these beneficial microbes till they can come into contact with the roots of the crop. This is one of the factors that improve the performance of our microbes when applied in a hostile soil environment which is generally deleterious to the performance of such products.

e) The fifth component is a product used as a foliar spray comprising nitrogen fixing bacteria (*Azotobacter chroococcum*) along with folic acid and thiazolidine carboxylic acid or its related compounds. This reduces the stress faced by the crop due to adverse climate, high temperature, poor soil conditions (including salinity and alkalinity), pests, disease.

f) The sixth component is a silicone based wetting and spreading agent cum penetrant which when mixed with other components viz component 3 and 5 respectively and water before a foliar spray i.e. to be used before component 5 and improves their rainfastness properties and penetration into the leaves, bark and other plant tissues for enhanced efficacy The wetting and penetrating agent is applied at 60-80 ml/200 liters of water ie 0.3-0.4 ml per liter of water/spray solution along with components 1, 2, 3 and 5.

The herein disclosed method of controlling infestation of citrus plants wherein the sequential use of these aforesaid components are based on a thorough study carried out on individual field situations to transform the disease affected orchards.

First the nano particle based formulation component (1) is applied as a soil drench and foliar spray. This is followed up by the simultaneous application of components (2) and (4). Thereafter the application of component (3) is carried out, as and when the citrus psyllid is observed at threshold levels.

Component (5) is applied from the onset of flowering at 30-45 day intervals ending with the arrival of the monsoons. The application of this component can be extended in case further improvement is required, usually 3-4 sprays between early February and July are found to give the desired results.

Component (6), which is a wetting and penetrating agent is mixed with components 3 and 5 when these are applied as foliar sprays before the application of component 5 at a prescribed dose of 60-80 ml/200 liters of water ie 0.3-0.4 ml per liter of water/spray solution.

In an exemplary embodiment, an agrochemical kit is provided, intended for controlling including management, preventing, removing and treatment mechanisms of the HUANGLONGBING (HLB), *Phytophthora* Infestation and various disease caused by bacterial and fungal pathogens. For preference, agrochemical kit comprises different doses of components 1 to 6 and an instruction for administration of the components of this agrochemical kit.

DETAILED DESCRIPTION

As per the studies, the HLB bacteria initially enter the crop roots and multiply, after which they enter the phloem tissue and spread through the entire plant. At the same time their disruptive activities in the roots that lead to tip dying attract another dangerous pathogen—*phytophthora* which is already present in the soil. *Phytophthora* resides in soil as a weak saprophyte wherever there has been excessive deposition of phosphates and other alkaline salts resulting in elevation of soil pH to 8 or 9. At these levels the natural enemies of this pathogen are in a weakened state. *Phytophthora* multiplies rapidly after entering the host tree and then it becomes more difficult to manage. Soil dwelling nematodes can also be significant factors that accelerate root decay and lead to the hastened death of the diseased tree.

Treatment Process a) The first component of the innovative technique is to loosen the grip of both pathogens on the crop by application of a potent biocide that is effective at extremely low doses. To make this basic ingredient, only naturally occurring substances are used and rely on the principle of the disruptive action of heavy metals on the metabolism and reproductive capability of disease causing microbe.

The principle of microencapsulation and finer particle size (near nano size) is used to achieve the objective of using the lowest possible doses. The concentration of the metals in the formulation is at ppm levels and when it is diluted in water and applied, this will be reduced to ppb levels. On entering the plant tissues it is likely to degrade and further reduced to practically undetectable levels.

The extremely fine particle size offers the advantage of not just low dose but also enable the product to reach inaccessible regions of the plant. This enables action at key sites and a rapid reversal of the infection. Since the phloem tissue is blocked, the deeper set xylem cells enable the product to be translocated rapidly to the growing root and shoot tips, once they reach these sites of infection the effect of their strong contact action begins to be noticed. There is a visible darkening of leaf colour as the yellow mottled leaves start to regain their normal appearance.

These nano particles also appear to have a salutary effect on the curling of young shoots caused by the feeding of the nymphs and adult citrus psyllids and the new leaves that emerge are bright green in colour, very shiny in appearance and bereft of disease symptoms.

The metals that can be used are those with proven biocidal action such as silver, copper, iron and more with combinations also possible.

This biocide is to be applied both as a soil drench as well as foliar spray. It works by preventing germination of fungal spores and preventing spread of the disease. Its effectiveness at low doses suggests some positive impact also on the mechanism of crop resistance which enable crops to withstand the attack of pathogens much better.

The critical reasons of the product appears to work so much better than conventional chemical fungicides are the nano sized particles which are able to pass through plant tissues and cell walls very easily and being metals, they pass relatively unchanged to the site where they encounter the pathogens.

The application as a soil drench enables the particles to reach the sites of infection rapidly through xylem tissue which are not blocked by the pathogens. The phloem and xylem tissue lie in close proximity to each other at the growing tips of the roots and shoots and the nano particles are able to reach the phloem and penetrate the masses of bacteria easily stopping the disease in its tracks.

Regular follow up foliar sprays serve to strengthen this effect and the revival of the tree startlingly quickly. Virtually every twig suffering from die back seems to herald the end of the disease by putting forth new buds just at the point where the disease had killed the tissue and new leaves and branches quickly grow to cover the bald spots. The colour and sheen of the leaves reveals that health has been restored. The old diseased leaves drop off quickly and are replaced by healthy new foliage that transform the appearance of the tree within a few months. There is a stark difference observed in the appearance of the emerging inflorescens. The new buds that emerge are pristine white in colour, compared to off white in the diseased plants. The dehiscing of buds is observable in the case of diseased trees, where relatively fewer buds transform into flowers. Brown specks can be observed on the buds, flowers as well as the empty spots in the inflorescens of the diseased trees.

b) The application of the nano biocide is quickly followed by the application of a microbial formulation containing plant growth promoting rhizosphere bacteria that get associated with crop roots in a symbiotic relationship.

The formulation can contain organisms that attack soil borne pathogens and also microbes that facilitate the availability of vital macro and micro nutrients through their biological action. These microbes are known grow rapidly with roots to increase availability of nutrients and release polysaccharides, antibiotics, fulvic and humic acids and plant growth regulators that increase the ability of the crop to withstand stress and disease. These also serve to reduce the soil pH to normal levels which is less suitable to *phytophthora* and more congenial to beneficial microbes. This product contains microbes that actively suppress soil nematodes further reducing the stress on the crop.

The formulation can contain microbes from among: *Thiobacillus, Trichoderma viride, T. harzianum, Bacillus subtilis, Frauteria aurantia, Azotobacter chroococcum, B. megaterium, Pseudomonas fluorescens Beauvaria bassiana, Metarhizium anisopliae*, Zinc solubilising bacteria, and many others jointly or singly.

The organisms are carefully chosen keeping in mind the multiple functions required to be performed right from suppression of *phytophthora* and nematodes to the HLB causal organism over an extended period to reduce the need for frequent application. The beneficial phytochemicals help to suppress *C. liberibacter* which can be seen by the sudden cessation of the symptoms of HLB like progressive die back of affected shoots and small yellow mottled leaves. The new foliar growth emerges below each and every dead twig, the buds give rise to fresh and luxuriant growth and within a few months the tree recovers completely with the new growth bereft of disease symptoms.

These organisms also improve soil conditions, by reducing soil pH and increasing agglomeration. This increases the moisture holding capacity of the soil and keeps it cooler enabling the crop to withstand moisture and temperature stress.

Another major benefit they provide is to regenerate the root system and help in the formation of vigorous new feeding roots which help the plants to meet the demand for nutrients and water.

By reducing pH to normal levels and increasing solubility of P, helping fix atmospheric N and increasing bio availability of K these microbes prevent the crop from facing a shortage of nutrients during critical stages of growth (including flowering, fruiting and fruit development) thereby helping its swift recovery.

It is observed that trees treated with this system seem to attract fewer psyllids for feeding and also egg-laying. The leaves appear glossier leading us to the conclusion that they will be less desirable to newly hatched nymphs. Similarly the quick reversal of the yellow green colouration of the leaves to a healthy darker green seems to make the trees less attractive to the psyllid.

This formulation out performs conventional chemical fungicides and offers salvation for the farmers in many ways.

Unlike chemical fungicides which are rapidly degraded after application, the living organisms in the product actually multiply, rapidly doubling in numbers every few minutes, thereby reducing the need for repeat application. In the first year just 2 applications a year is needed, which could reduce to just a single annual application from the second year onwards as populations of the beneficial microbes build up.

These microbes constantly evolve to remain a step ahead of the pathogens they compete against, so there is no problem of resistance and the need to resort to increasingly more expensive patented chemicals. Countless millions of poor farmers all over the world will benefit. As informed before, conventional antibiotics are harmful to the plant and cannot be used, however, the phytochemicals (including antibiotics) produced by the product are not harmful and actually help the crop which is evidenced by the extremely good quality of the leaves and produce. Record yields are achieved by a whole range of crops benefiting from this treatment and not just citrus.

A new variant of this product includes a foliar spray so that any spores of the pathogen that are deposited on the foliage can also be subdued with only a few applications a year.

c) The third component comprises an unique formulation containing plant derived amino acids, cytokinins, humic and fulvic acids together with a N fixing microbe is added simultaneously to make the soil more amenable to the growth of the microbes in the soil. This product formulation has proved highly effective as it also provides the plant with much needed 'N' for production of protein that helps the plant to create amino acids to fight the disease.

This product works in a synergistic manner with the other products mentioned above and encourages the rapid growth of microbes enabling it to outstrip conventional products in terms of performance.

For instance trials carried out with both products applied at the time of sowing in some annual crops show a rapid development of the roots within 15 days after germination compared to crops grown using conventional chemicals alone. Root growth is 2-3 times greater and shoots are stronger and able to withstand high temperatures as well as disease like damping off (caused by Fusarium) much better. A 20% higher germination percentage has been observed and crop stands are much better enabling farmers to reduce seed rates and save money. Leaf area and chlorophyll content is better and crops treated with the disclosed method are able to overhaul crops planted 2 weeks earlier in terms of appearance (root development, height, leaf area etc) within a month after sowing.

d) Further the citrus psyllid is controlled by a fourth component which is formulation based on a plant extract that can contain oils like neem, karanj, soap nut, custard apple, lemon grass, clove oil, citronella, ginger and the like having some insecticide repellent properties either singly or in combination with one another. On application it is observed that the citrus psyllid adults and nymphs stop feeding and die. The product interferes with the moulting of the nymphs causing mortality and failure to advance to their next stage of development.

Another advantage of this application that has been observed is the reduction in sooty mould, which shows that the nymphs and adult psyllids have stopped feeding almost immediately after application.

The application of natural oils such as those used in the product help overcome the problem of resistance to chemical insecticides as they contain a cocktail of natural alkaloids.

e) All sprays are applied along with a silicone based super spreading and penetrating agent presently introduced as component-6. This product is extensively tested by leading Government research organisations of India over several seasons. Its use enables better penetration of the products through the bark as well as better spreading and rain fastness, these result in a more economic use of the product due to better efficacy.

f) Another problem encountered due to disease is an increased dropping of immature fruits due to the weakened state of the crop and its inability to withstand high temperatures in the summer months. The shortage of vital photosynthates in the twigs which provide the much needed energy for the developing fruits is one problem. The second problem is the inability of the root system which too is starved of nutrients (due to blockage of phloem) to grow and provide the moisture and dissolved minerals to the plant. This is due to death of root hairs and growing root tips caused by HLB.

Another problem caused by such stresses is the uncoiling of protein structures which provide strength, such as the stalks of flowers and fruits. When the plants are unable to generate enough proteins and amino acids to sustain their flowers and fruits, these drop to the ground.

The application of a product (component 5) containing an amino acid as well as a precursor for a second, helps overcome these problems by enhancing the activity of the metabolic pathways of the plant that help combat moisture stress and disease. The activation of the proline pathways to increase the concentration of this super solute in the plant sap reduces loss of moisture and helps retain turgidity of cells required for preventing senescence and fruit dropping. This product increases the ability of the plant to withstand temperature stress and resist the uncoiling of protein structures thereby enabling the retention of more flowers and fruits and increasing yields as well as quality of produce.

This product further increases pollination and thereby fruiting. Pollinators can sense the presence of proline in nectar which is required by them to power their flight muscles, so increased presence of this amino acid ensures greater visitation of such flowers by pollinators especially early in the morning for their first daily flights when their energy levels are at their lowest.

Proline is a short chain amino acid, also known as imino acids which contain sulphur, these are also activated by trees when confronted with disease and are responsible for developing natural resistance.

The success of this system lies not just with the 6 carefully selected products but also in their timing and sequence of use. The treatment is started when the citrus plant is naturally at its most vigorous stage of growth and the treatment accelerates these processes resulting in the reversal of the course of this deadly disease and both pathogens as well as the vector.

This method encourages the plant's natural defences and uses the synergism of the microbes to ensure the continuous production of beneficial phytochemicals that further encourage this property.

g) Introduction of a concentrated mycorrhizal formulation with added bio catalysts for increasing efficiency of crop root system (in component 2) is a part of the process which needs to be applied just once a year. Global warming leading to rising temperatures and lower rainfall leads to a strain on the root systems of crops to absorb nutrients and moisture. This means that more energy needs to be expended by crop roots, leading to reduced amounts available for flowering and fruiting. Together with deteriorating soil conditions mentioned earlier, this is another reason why yields have stagnated.

Mycorrhizae also protect plants from attacks by pathogens and mobilise critical nutrients like P and K as well as micronutrients. Significant savings in fertilizer application costs can be achieved by farmers.

By introducing a concentrated formulation of endo mycorrhizae in the disclosed method and kit, the twin objectives of healthy crop and soil is achieved together with increased yields.

These advantages have enabled the disclosed method with crop specific variations to be used with success in many other crops such as capsicum, cotton, rice, wheat, chillies, potatoes, capsicum (bell pepper), tomatoes, onions, carrots, cucurbitaceous crops, pulses and many others with resounding success.

This system has proved useful in controlling not just HLB and *Phytophthora* but also other fungal organisms like *Fusarium, Rhizoctonia, Alternaria, Magnoporthe grisea, Peronospora, Puccinia, Cercospora* and many others.

This system has also worked well against bacterial diseases like *Xanthomonas, Pseudomonas* and others.

The system has also provided significantly superior results in deterring pests like mites, whiteflies and thrips in various crops.

However it has provided unprecedented suppression of viral diseases which cannot be controlled by any chemical pesticide. The various viral diseases against which it has proved successful are yellow vein mosaic and leaf curl virus which affect solanaceous crops, cucurbitaceous crops as well as pulses, cotton and many others.

Silver Nano Product Formulation

The production of nano silver particles is an established science. The product differs in the formulation, where activity is enhanced using hydrogen peroxide at a concentration of 2.5% and using additives and stabilisers for a more stable product. The size of the nano particles is anywhere for 1 nM to 100 nM's but is maintained within a range of 1-10 nMs by regulating the current. The aqueous solution of nano silver particles is concentrated to a level of just 50 ppm-100 ppm and it can be diluted to any concentration desired by adding deionized water. Citric acid has been used to reduce the pH range between 2 and 3 and reduce volatilisation of $H_2O_2$.

Silver is a powerful germicide, however the nano particles make it much more effective at low doses because these tiny particles can pass very easily through cells and reach the site of infection. The fact that these are effective at infinitesimally low concentrations gives the disclosed method a big advantage over chemical fungicides which are required to be used at much higher concentrations in order to be effective.

What is not commonly known is that the bacteria responsible for HLB resides in the roots for a few years before it builds up its population and then grows onwards through the phloem cells till it infests every emerging shoot or root hair. Phloem cells are critical for passing nutrients (photosynthates) produced by leaves to the growing tips of the plant. Since these delicate and small parts of the plant have relatively few phloem cells and low stored energy, they are the first to succumb to the infection.

Since roots are not visible to the farmer, the first symptom of the disease he sees is the die back of the young shoots and erroneously assumes this to be caused by *Phytophthora* and commences fungicidal application.

As explained earlier, the dying roots attract secondary infection by the fungus like organism—*Phytophthora*, another deadly plant pathogen. This also grows upwards through the dying tissue and later infects the entire plant. Symptoms are seen in the form of oily secretions emanating from the main stem and branches. This disease can cause death of the tree once it girdles the phloem tissue all along the circumference of the main stem or branches. The HLB bacteria have evolved to attract an insect vector, in this case the Asian Citrus Psyllid which is attracted to yellowish colouration of citrus leaves. It is believed that trees infested by this disease also release chemical signals which are also attractive to these vectors. The HLB bacterium causes the leaves of the infected tree to turn yellow and release the chemical signals which attract the psyllid in large numbers enabling the bacterium to spread to healthy trees.

What is also not realised is the nature of the plant's defence mechanism, which relies on the formation of free radicals like nascent oxygen to kill pathogens and also the surrounding tissue which has been infected. The pathogen requires living tissue to proliferate, by killing the surrounding tissue; the plant is able to limit the infection to a very small area. The nascent oxygen quickly kills the pathogen in this encircled tissue which dries up and drops off, freeing the plant from the clutches of disease. By adding hydrogen peroxide to the nano silver formulation and applying this to the plant, several purposes are served:

a. The nano silver particles proliferate through the plant tissues especially the roots where they are drenched, reducing the load of inoculum present so there are fewer bacterial cells available to proliferate.

b. They also serve to reduce the intensity of attack of *Phytophthora* c. Silver nano particles are also carried upwards through xylem tissue till they reach the very tips of the dying shoots where they come into contact with the bacterial cells killing them d. The foliar spray enables silver nano particles to pass through infected leaf tissue where bacterial cells are destroyed.

e. The application of hydrogen peroxide in small quantities stimulates the plant's defence mechanism to release more nascent oxygen through a complex physiological reaction involving a series of enzymes. This magnifies the impact of even a single application several fold, enabling the plant to show quick recovery.

f. The destruction of bacterial cells and the stimulation of the plant's defence mechanism enable the tree to reverse the symptoms of disease. The leaves quickly turn green reducing its attractiveness to the insect vector thereby relieving the secondary damage caused by the insect.

This formulation is the first measure to be used in the said systematic procedure. Soil drenching with the nano silver product is done after preparing the base of the trees receiving the drench for maximum impact. A light irrigation is given in advance so as to reduce the quantity of product required for drenching, depending on the soil type watering 3-4 days in advance of the activity is generally sufficient. The dampness of soil also facilitates easy weeding which is a prerequisite to remove any space for the pathogens to seek shelter.

The best time for initiation of treatment is before flower initiation. In India this is usually the month of February. This will enable farmers to save their crop in the current season/ year. The second best time is after the onset of monsoons usually July as this will enable the plants to recover faster and give a much better crop in the next year. Monsoons are also a time when the plant is geared towards producing more leaves and shoots so at this time the procedure enables the plant to recover faster. The rainy season is also favourable for the growth of the beneficial soil microbes since soil temperatures are lower and moisture is adequate.

On DAY ONE: A circular berm of 6" height is prepared around the tree trunk. The area of this berm should encompass the area shaded by the canopy of the tree for maximum coverage of the roots. All weeds within the circumference are to be uprooted and removed from the site. A light irrigation is given so as to raise soil moisture content.

DAY 4: The nano silver formulation is to be used at 10 ml/liter of water and depending on the size of the tree, 15-20 liters of spray solution is to be used for drenching the root zone of each tree. In effect 150 ml-200 ml of the product will be used for each tree. Soil drenching will be required just once a year, sometimes depending on the observed recovery, a second application might never be required.

DAY 4, 34, 64 & 94: A foliar spray is repeated at monthly intervals in heavily infested citrus orchards for 3-4 months to remove any vestiges of infection. The product is applied at 5 ml/liter of water with the addition of a special wetting agent also developed by us containing a concentrated mix of trisiloxane super spreading and penetrating agents. This enables the product to even penetrate bark. This super spreading and penetrating agent is mixed with the spray solution at a concentration of 0.25-0.4 ml/liter of water. Generally 5-6 liters of spray solution is enough to cover a tree but larger volumes can be used on larger trees for thorough wetting.

The super spreading and wetting agent also helps prevent the product being washed off during rains, rendering the disclosed method flexible enough to be used even if there is a break for 2-3 hours in the rain.

Microbial Consortium

The microbes which are used are commonly available soil dwelling rhizosphere microbes which are commonly available as standalone products and are made by many companies. Since the objective was to keep the cost of treatment low, we have used such microbes that are easily available off the shelf. What is unique about this product is the combination of microbes selected, each with different characteristics serving different purposes that have never before been used together to address the entire set of complex issues that prevent farmers from raising a good crop and making profits.

This product formulation is also unique because of the high concentrations of microbes used. This enables greater efficacy at lower doses and improves the survival chances of microbes under inimical soil conditions.

A dextrose carrier has been used for manufacturing this concentrated formulation instead of talc so as to provide readymade energy for the growing numbers of beneficial microbes.

The product can be modified based on an analysis of the soil in different parts of the country to address specific issues that can come up. A standard product could contain in any combination the following organisms:

*Azotobacter chroococcum, Frateuria aurantia, Pseudomonas aeruginosa, Bacillus subtilis, Trichoderma viride, Pseudomonas fluorescens, Bacillius megaterium, Bacillus mycoides, Metarhizium anisopliae.* The concentration of microbes in the formulation would be between $1 \times 10^8$ to $1 \times 10^9$ cfu's/gram. In addition, the consortium can also include a high concentration of endo mycorrhiza with a formulation strength of 50,000-150,000 infective micropropagules per gram of the product.

Depending on the soil and crop, the products can be formulated containing a single or different multiple combinations of the above microbes for reducing cost of application and increased specificity.

The purpose behind this product is to address the problems posed by HLB, *Phytophthora*, deteriorating soil conditions caused by the present method of agriculture and nematodes that can aggravate the intensity of disease infection.

HLB is caused by bacteria that cannot be controlled by the application of fungicides, which is the common practice resorted by farmers in India assuming this to be an attack of *Phytophthora*.

HLB can be controlled by antibiotics which are expensive and require to be injected in the stem which makes their use even more laborious. However the major problem posed by the use of antibiotics is their innate phytotoxicity to citrus.

The deep seated nature of HLB necessitates the use of a heavy dose of antibiotics which can injure and even kill the citrus tree.

As explained earlier, secondary infection (through roots injured by HLB) caused by *Phytophthora* compounds the problem, a tree weakened by HLB is easy prey to *Phytophthora*.

Plant nematodes are soil dwelling pests which also cause serious damage to roots of citrus and lead to secondary infestation by fungal pathogens. Commonly used chemical nematicides are expensive and highly toxic.

The higher soil pH and excessive phosphates also suppress the availability of micronutrients like Zinc which are essential for crop growth. Plants weakened by the deficiency of micronutrients are more susceptible to disease.

The use of heavy farm machinery for intercultivation destroys soil structure and creates a hard pan at a depth of 10-12" beneath the soil surface. This coupled with the low soil organic content of soil results in periodic waterlogged conditions (during flood irrigation and rain events) that favour *Phytophthora* and other soil pathogens. Reduced soil moisture holding capacity arising from a destruction of soil structures can accentuate the impact of drought and erosion of this irreplaceable resource.

This is accentuated by global warming which is resulting in periods of heavy rain interspersed with periods of high temperature and near drought conditions.

The disclosed microbial consortium has been evolved after a thorough study of all these problems and offers the following benefits:

a. Antagonistic agents of *Phytophthora* and other soil pathogens have been incorporated which suppress these pathogens by antibiosis, predation and parasitisation. Under favourable conditions, they grow much faster than the pathogen and occupy the soil areas near the roots creating a barrier to pathogens. Chemical signals released by the pathogens encourage these microbes to grow towards their colonies and suppress them.

b. They chelate nutrients making them unavailable to pathogens yet available to crop roots, reducing the problem of micro nutrient deficiency.

c. In a symbiotic relation with crop roots, they continually release a range of beneficial phytochemicals like humic and fulvic acids, antibiotics, growth regulators, cytokinins, auxin and gibberellins that encourage roots to grow faster. They release polysaccharides that bind soil particles creating air spaces for root aeration.

d. This continual release of organic material increases soil organic content and restores soil texture and fertility and also prevents erosion.

e. Increased moisture holding capacity enables the soil to remain much cooler which benefits the crop immensely and reduces loss of water and nutrients due to leaching.

f. They improve the availability of major nutrients like N, P and K which the tree was unable to access due to damage to the root system caused by the pathogens. These enable the tree to fight the disease.

g. Through better root growth, they improve the ability of crops to withstand periods of high temperature and drought much better than conventionally raised crops.

h. These microbes also suppress nematodes thereby preventing root damage and secondary infection by pathogens.

i. The addition of high concentrations of endo mycorrhizae helps improve the efficiency of roots in drawing nutrients by 10 to 100 times, thereby enabling them to withstand stress conditions far better. This allays the adverse effects of disease as well.

j. New root growth enables the infected tree to draw more nutrients and reverse the weakness caused by root decay caused by the pathogens.

This product is applied in the following manner:

Day 9: Five days after the application of the nano silver product as a soil drench, the microbial consortium is applied at a dilution of 1.5 to 2 grams in 20 liters of water in the same manner as stated above for the nano silver product.

If the first application is given in February, the response of the citrus trees are observed and a second application given after 150 days in the month of July with the onset of the monsoons. If the response after the first application is good, then a second application may not be required.

Plant Extract

Solvent extracts of *Derris Indica* also known as *Pongamia* or Karanj plant were tried out on a small scale against sucking insect pests on a range of crops and found to have beneficial properties. The oil from the seed of this plant seed of Karanj plant contains the highest content of the active principles which are primarily plant alkaloids and flavonoids.

The product is made by a conventional solvent extraction process used for any oil seed. The seed kernel is subject to reaction with organic solvents and the main active ingredient, karanjin is isolated. However in order to retain the advantages of the natural product, 30% by weight of the oil that was extracted is incorporated in the formulation. The active principle—karanjin that was isolated earlier is also incorporated at a concentration of 2%-3%.

This combination of active principle and oil is dissolved in a petroleum solvent and a non ionic wetting agent is added to give a stable formulation containing not just the active ingredient—Karanjin, but also other alkaloids and flavonoids present in the natural oil.

The disclosed product offers the following benefits over conventional chemical pesticides:

a. Being a natural product, it does not leave harmful residues.

b. The presence of a cocktail of natural alkaloids and flavonoids with different modes of action reduces the risk of the development of resistance.

c. Though this is a natural product, damage caused by the psyllids and other sucking pests like white flies can be stopped immediately through its anti feedant action.

d. It is known that Karanjin also works by preventing moulting. This prevents the insects from growing to their next stage. Psyllid nymphs are unable to transform into adults and this breaks the life cycle of the insect and reduces pest pressure.

e. Its gentle healing action reduces stress exhibited by plants with chemical insecticides and leaves remain green unlike the dry yellow appearance they take on after repeated chemical insecticide sprays.

f. Unlike most chemical pesticides, this product does not harm predators and parasites of the psyllid making this most amenable for. IPM (Integrated Pest Management).

g. Citrus psyllids do not merely infect healthy plants with disease, during the course of their feeding; they release toxins (and possibly viruses) into the growing tips of the citrus trees. This causes the leaves to curl and new shoots remain stunted, this has a direct impact on flowering and fruiting.

h. These psyllids and their nymphs also release a secretion called honey dew which covers the leaves and attracts the sooty mould fungus which forms a black mat on the leaf surface, completely blocking sunlight and stopping photosynthesis which weakens the plant further.

i. This accentuates the yellowing of leaves and attracts even more psyllids to congregate on such trees magnifying the problem and helping the spread of disease.

j. The disclosed system takes cognizance of all these complex variables and delivers benefits rapidly by:

Enabling the leaves to regain their lustrous green colour thereby discouraging psyllids from congregating there This return to health and increased chlorophyll content helps the plant to photosynthesize and regain its health rapidly Preventing the formation of the mat of sooty mould and encouraging photosynthesis Neutralises the toxins and viruses injected by these pests and enables new healthy growth to emerge bereft of any disease symptoms Increased flowering and fruit setting is observed whenever the system is implemented in time This product is dissolved in water at a concentration of 2-2.5 ml per liter of water and the super spreading agent and penetrant is added at 0.25-0.4 ml per liter of solution. This product is applied during periods of peak flush of citrus (when new leaves emerge) since this is when the citrus psyllid is most active, attracted by the pale yellowish green coloration of diseased leaves as well as new flush.

Applications are synchronised with the observation of psyllids in the orchard when their populations are at Economic Threshold Levels (ETL's) these can vary from country to country.

Granular Formulation Containing Beneficial Phytochemicals of Plant Origin

Most agricultural soils contain low organic content due to decades of excessive reliance on chemical inputs and mechanisation. The excessive presence of salts arising from chemical fertilisers and irrigation using ground water having salt content is inimical to the soil ecosystem and result in the problem of soil salinity. Often these salts can result in an increase in soil pH and result in soil alkalinity. Both conditions cause a marked reduction in the presence of beneficial microbes and render such soils unfit for cultivation.

If biological products are used in such soils, the survival of the beneficial organisms contained therein is doubtful; so the results obtained from the use of such products will be far from satisfactory.

This problem has been overcome by incorporating a granular formulation that provides
a) humic acid
b) amino acids
c) cytokinins These products are made from enzymatic extraction from vermicompost, plants and sea weed respectively. These are available off the shelf as standalone solo products. The unique formulation is the use of all 3 components together in a concentrated form reducing the dosage requirements by 40-50% per acre and result in significant cost reductions for the farmer.

By applying this along with the soil microbes, we are encouraging their growth which in turn helps root growth and a substantial increase in soil exudates. This product effectively kick starts this beneficial cycle rapidly restoring soil conditions and ecological balance.

This product comprises all three basic constituents coated onto double roasted bentonite clay granules with a concentration of 15-20% by weight. Application of these ingredients on to the granules can be by means of spray or mechanical mixing using a drum mixer. The bentonite granules play a crucial role in product efficacy as they absorb these products and release them slowly in the soil in the presence of adequate soil moisture in the root zone, preventing excessive release and leaching.

This product can also be supplied as a soluble powder formulation in concentrated form which is preferred for long distance transportation where logistics costs are a significant factor.

This product is applied along with the microbial consortium mentioned earlier so that soil conditions are rendered more amenable for the growth of the beneficial microbes present therein. Even the standalone products are applied primarily for crop growth and never intended to be used along with microbial consortia.

Foliar Spray Comprising Nitrogen Fixing Bacteria Along with Buffer

The disclosed product contains a high concentration of N fixing bacteria, *Azotobacter chroococcum* present in a concentration of $1\times10^8$ to $1\times10^9$. The addition of the buffer enables a rapid proliferation of the beneficial microbes present and improved product efficacy.

N is an important macro nutrient that is a constituent of proteins, amino acids, nucleic acids, vitamin and other important building blocks of the plant.

Without the presence of N, plants would not be able to grow new leaves. The ability of leaves to photosynthesize is severely impaired in the absence of N.

Protein is an important constituent of load bearing structures such as the stalks of flowers and leaves. A shortage of N results in flower and fruit dropping and thereby reduced yields.

N applied as a chemical fertilizer is highly susceptible to leaching, this results in an apparent shortage during critical stages of crop growth. This foliar spray mitigates these problems and ensures a steady supply even during critical stages of growth like flowering and fruiting.

In order to improve the efficacy of the N fixing microbes, a buffer is provided which contains carboxylic acids like thiazolidine carboxylic acid (TCA) or carboxylic acids that are acetylation by products of TCA along with folic acid in a ratio of 5%:0.1% respectively.

This product is a unique combination of microbes and buffer and is seen to provide several benefits which include:
a. Reduced fruit and flower dropping
b. Better quality of produce
c. Increase drought tolerance
d. Improved growth of microbes present and improved product efficacy
e. Increased secretion of amino acids by the tree especially sulphur containing amino acids like proline are believed to help in fighting disease
f. Proline also attracts pollinators which improves fruit set
g. Higher presence of N in leaves also helps them to turn green faster thereby reducing the attractiveness of the tree for egg laying by the citrus psyllid. This in turn reduces the population of nymphs on the tree and reduces the risk of secondary infection.

The said product is applied during periods of excessive heat and dryness usually between March and June which also coincides with flowering and fruit initiation. Sprays are continued at intervals of 30-45 days depending on agro climatic conditions. A maximum of 3-5 sprays may be given during the course of the year.

If the botanical extract of Karanjin has been applied earlier, it is advised that this product be applied after a gap of 15 days.

Observations

A reversal of symptoms is observed within 3-4 weeks after application of the 2nd step on day 9. The progression of the disease is seen to stop and the branches put forth new buds showing the infected area is regaining its health.

Three months after Step 2 and application of all other intermediate steps listed above, it is observed that the bald patches of the tree are getting covered with new branches.

Improved flowering and visitations by pollinators is observed

Restoration of the environment is seen by increased presence of predators like spiders and beetles which prey on the sucking pests like the psyllid and its nymphs.

Shoot growth is seen to be rapid and leaves emerging from the new shoots are healthy and shiny. The chlorophyll content of the leaves appears to be much higher and the leaf size is 2-3 times larger than the diseased older leaves.

Increased flowering and pristine white coloration of buds and flowers is observed in contrast with mottled disease infested buds and flowers seen in conventionally raised crops. Flower dropping is visibly reduced and fruit setting is heavy.

It is observed that yields reach pre infestation levels in the same year if treatment is done in February and increase further in the 2nd year with a continuation of the treatment.

Trials:

Several field trials have been conducted over the years in North India and 2 examples are given herewith TRIAL 1 Village Lilawali, District Hanumangarh, Rajasthan.

A severely infested orchard was selected after confirming symptoms of HLB and *Phytophthora*. The incidence of disease was so severe that the farmer was contemplating uprooting his entire orchard. Income was Rs 30,000 ($517) from the entire orchard for the year.

Number of trees: 600 with 100% infestation.

Trial commenced June Observation by December: Almost 80% recovery with 482 trees having completely recovered and in good fruit bearing condition 95 trees, 15% of the population were on the way to recovery with partially girdled branches still showing disease symptoms and 23 trees or about 4% of the trees were too diseased to recover and had to be uprooted.

Income increased to Rs 3 lacs for the year (approximately $5000)

Diseased branches were pruned and trials continued for a second year

Observation December

Remaining 577 trees appeared to be almost completely recovered and farmer reported increased income to Rs 5 lacs (approximately $8600)

Trees started showing fresh growth within 2 months after applying $2^{nd}$ STEP

Leaf size was much larger and leaves were shiny without mottling symptoms

Leaf curling due to psyllid feeding was absent

Very few leaves showed traces of sooty mould fungus, indicative of low infestation by citrus psyllids Large number of spiders and webs seen with insects trapped showing a restoration of the ecological balance of the orchard Fruit quality was good and fruits were larger in size.

Trial 2

Village Lakhian (5-O), District Sri Ganganagar

The farmer had grown citrus over 1.25 hectares and his income had decline from Rs 250,000 ($4300) in 2012 to Rs 130,000 ($2240) in 2013. He was assuming further deterioration and the prospect of having to uproot his orchard. All trees showed symptoms of HLB and 80 trees exhibited *phytophthora* gummosis.

The trial started in February with the farmer agreeing to take up the complete system of treatment. Out of a total of 312 trees, 263 had survived.

The $1^{st}$ observations were taken on end March and all trees had recovered remarkably well within a month of the $2^{nd}$ STEP. Heavy flowering was observed with increased bee visitation.

Application of STEP 3, 4 and 5 proceeded on schedule and heavy fruit bearing was observed. There was some damage to fruits caused by hailstorms in May leading to some losses but the progress of the orchard was clearly visible.

No HLB symptoms were to be seen on the leaves, there were no bald patches in their crowns (indicative of die back) by end May.

An attractive bid of Rs 4,10,000 ($7,100) was received by the farmer in June for his orchard, an increase of income 215% over the previous year.

Although the foregoing description of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

What claimed is:

1. A method of controlling at least one of bacterial, fungal, viral nematode and insect infestation of a crop comprising the steps of:

i) application of a first component as a soil drench and foliar spray followed by simultaneous application of a second component and a fourth component followed by application of a third component, as and when an insect pest is observed at threshold levels;

ii) application of a sixth component which is a silicone based wetting and spreading agent and penetrant mixed with the third component and a fifth component and water as foliar spray; and iii) applying the fifth component as a foliar spray from an onset of flowering of the crop at 30-45 day intervals;

wherein:

the first component includes a water based formulation containing nanoparticles of silver alone in microencapsulated form or in conjunction with either 2.5% hydrogen peroxide or nanoparticles of a metal;

the second component includes a consortium of plant growth promoting rhizosphere microbes which occur in nature;

the third component includes a plant extract which is an oil extracted from the seed of Karanj (Pongamia glabra/Derris indica);

the fourth component includes a slow release, granulated formulation or Soluble Powder (SP) formulation comprising amino acids, sea weed extracts, humic and fulvic acids which arc extracted from compost;

the fifth component includes nitrogen fixing bacteria along with folic acid and thiazolidine carboxylic acid; and the sixth component includes a silicone based wetting and spreading agent and penetrant which when mixed with the third and fifth components and water is applied as a foliar spray.

2. The method according to claim 1 wherein the first component further includes citric acid thereby reducing a pH range to between 2 and 3 and reducing volatilization of $H_2O_2$.

3. The method according to claim 1 wherein nanoparticles of the first component are sized in a range of 1-100 nm.

4. The method according to claim 1 wherein the second component further comprises micropropagules of different species of the endo mycorrhiza Glomus, and wherein the consortium of plant growth promoting rhizosphere microbes fix Nitrogen (N).

5. The method according to claim 4 wherein the micropropagules of different species of the endo mycorrhiza Glomus are selected from the group consisting of G. mosseae, G. intraradices, G. aggregatum, G. microaggregatum, G. fasciculatum and G. etinucatum.

6. The method according to claim 4 wherein the consortium of microbes is used either as a single product or divided into two components containing mixtures of rhizosphere microbes.

7. The method according to claim 4 wherein the rhizosphere microbes in the second component are Pseudomonas fluorescens, Bacillus subtilis, Bacillus mycoides (the fungus) Trichodema viride occurring in nature.

8. The method according to claim 4 wherein the concentration of each of the microbes in the second component is between $1\times10^8$ and $1\times10^9$ CFU per gram, except the endo mycorrhiza which is present at a concentration in a range 50,000 to 150,000micropropagules/gram.

9. The method according to claim 1 wherein the third component is an oil extracted from seed of Karanj (Pongamia glabra/Derris indica) as an emulsifiable concentrate comprising 2% alkaloids extracted from the oil in semi purified form together with oil ranging from 25-35% formulated with petroleum solvents.

10. The method according to claim 1 wherein the fourth component is a slow release, granulated formulation and slow release of the granulated formulation is ensured by incorporating constituents of the formulation in double roasted bentonite granules with a coating of any natural polysaccharide or natural or synthetic polymer.

11. The method according to claim 1 including repeating the steps i) through iii) three or four times between early February and July.

12. The method according to claim 1 wherein the infestation of the crop is by at least one disease selected from the group consisting of Huanglongbing (HLB), Phytopthora citrophthora, Phytophthora Gummosis, Xanthomonas, Pseudomonas Asian Citrus Psyllid, Diaphorina citri Kuwayama and soil dwelling pathogenic nematodes.

13. The method according to claim 1 wherein the infestation of the crop is caused by pathogens on crops selected from the group consisting of potato, tomatoes, egg plants, bell peppers, oil palm, durian, black pepper, blue berries, capsicum, cotton, rice, wheat, chilies, onions, carrots, cucurbitaceous crops, pulses and forest trees.

14. The method according to claim 1 wherein the infestation of the crop is caused by soil borne pathogens selected from the group consisting of Rhizoctonia, Fusarium, Aspergillus, Macrophomina, Pythium, Scerotinia, Verticillium, Alternaria, Magnoporthe grisea, Peronospora, Puccinia, and Cercospora and the crops selected from the group consisting of strawberry, cole crops, celery, spinach, cucumber, melons, squash, beans and peas.

15. The method according to claim 1 wherein the infestation of the crop is caused by an insect pest or nematode, wherein the insect pest is selected from the group consisting of mites, whiteflies and thrips.

16. The method according to claim 1 wherein the infestation of the crop is caused by a disease selected from the group consisting of yellow vein mosaic and leaf curl virus, and the crop is selected from the group consisting of solanaceous crops, cucurbitaceous crops pulses and cotton.

* * * * *